United States Patent [19]

Woodley et al.

[11] Patent Number: 4,697,599
[45] Date of Patent: Oct. 6, 1987

[54] APPARATUS FOR LOCATING AND DETECTING PAIN

[76] Inventors: William Woodley, Unionville; David Longmire, Hamilton, both of Canada

[21] Appl. No.: 827,453

[22] Filed: Feb. 10, 1986

Related U.S. Application Data

[63] Continuation of Ser. No. 599,182, Apr. 11, 1984, abandoned.

[51] Int. Cl.[4] ............................................. A61B 5/05
[52] U.S. Cl. .................................... 128/734; 128/639
[58] Field of Search ............... 128/734, 735, 723, 693, 128/639; 324/57 R, 62, 65 P; 273/1 E

[56] References Cited

U.S. PATENT DOCUMENTS

| | | | | |
|---|---|---|---|---|
| 3,848,582 | 11/1974 | Milani et al. | ......................... | 128/639 |
| 3,894,532 | 7/1975 | Morey | ................................... | 128/734 |
| 4,184,486 | 1/1980 | Papn | ..................................... | 128/734 |
| 4,375,219 | 3/1983 | Schmid | ................................. | 128/639 |

OTHER PUBLICATIONS

Yomamoto et al, "Dynamis System for Measurement of Skin Impedance", Mic & Biol. Eng. & Comput. 1979, vol. 17.

Machlin, "Thoracic Impedance of Human Subjects", Mic. & Biol. Eng & Comput., 1978, v. 16.

Kaul, "Skin Resistance Biofeedback", C & R, 1980.

Primary Examiner—Edward M. Coven
Attorney, Agent, or Firm—Wegner & Bretschneider

[57] ABSTRACT

A selective tissue conductance meter is described which can be used to assess pain, abnormal sensation or sympathetic dysfunction in a human being or animal. Two concentric electrodes are mounted in fixed relative relationship on a housing which is capable of being held in one hand of the user. Contained in the housing is an electric circuit connected to the two electrodes, which circuit produces an electrical signal having a pulse frequency that varies according to the measured conductance. A battery capable of providing low voltage power is connected to the circuit. Several devices are disclosed for monitoring or measuring the electrical signal to permit the user to detect the pulse frequency of the signal. One such device comprises an audio circuit capable of producing an audible sound or click for each pulse of the electrical signal. A liquid crystal display can provide a digital readout of the number of pulses covered over a short time span.

20 Claims, 7 Drawing Figures

APPARATUS FOR LOCATING AND DETECTING PAIN

This application is a continuation of Ser. No. 599,182, filed Apr. 11, 1984, abandoned.

BACKGROUND OF THE INVENTION

This invention relates to devices for measuring or diplaying an electrical characteristic of living tissue such as that of a human being or animal. Various methods and machines have been used in the past to measure and/or display certain electrical characteristic of living tissue. The purposes of such measurements included detection of increases or decreases in, for example, resistance of the skin, which were shown to occur during fluctuations in autonomic nervous system activity. Transient decreases were used by physiologists and pyschologists as indicators of increased autonomic function and anxiety. Clinical neurophysiologists on the other hand have measured for increases which would help them localize areas of skin in which the normal nerve supply had been damaged or disrupted.

For example, in the paper published in 1945 by Curt P. Richter entitled "Instructions For Using The Cutaneous Resistance Recorder or "Dermohmeter" On Peripheral Nerve Injuries, Sympathectomies, and Paravertebral Blocks" it was recognized that the resistance offered to the passage of a minute direct current through the body is localized almost entirely in the skin. A puncture made through the skin with a hypodermic needle reduces the resistance from any level practically to zero, no matter how high it was for the previously intact skin. The resistance over an abrasion or cut is likewise low. It was also recognized that skin resistance is controlled largely through the nervous system. The paper describes a small portable dermohmeter consisting of a micrommeter a $4\frac{1}{2}$ volt battery, potential divider and a telephone plug socket furnished with a jack switch. Two silver-plated phosphor-bronze electrodes were connected by an insulated line to the panel of the dermometer. One of these electrodes was constructed so that it could be clipped to an ear lobe while the other had the shape of a hammer with a large disc at one end of the head and a small disc at the opposite end. The current from the battery passed from one electrode to the other by travelling through the body of the patient and through the microammeter. The potential divider was used to regulate the amount of current that flowed from the battery through the patient. With the potential fixed, the amount of current registered by the microammeter depended on the resistance offered by the patient's skin to the passage of the current. It was suggested in the paper that the patient should be prepared before use of the instrument by exposing him to external heat for a few minutes. It was also necessary to prepare the patient by cleansing the ear lobe and pricking the skin thereat with a hypodermic needle to eliminate the skin resistance. A special paste or electrode jelly also had to be used on the electrode that was to be fastened to the ear lobe.

Also in a paper published in 1945 by Captain H. Jasper and entitled "An Improved Clinical Dermohmmeter" a different type of dermohmeter, which was recommended for Canadian service, is described. It was mounted in a wooden box measuring approximately eight inches in each direction and weighing seven pounds. It requires the use of nine standard $1\frac{1}{2}$ volt flashlight batteries, a 0–50 microammeter with a special contact, a special switch and seven fixed resistors. The specifications in the paper indicate that a current of up to 500 microamperes could be reached as the voltage is increased.

U.S. Pat. No. 2,799,269 illustrates an electropsychometer having two meters one of which registers continuously the electrical ohmic resistance existing between the skin contacting elements of a special electrode. This electrode had separate cylindrical elements mounted on a non-conductive member and the entire electrode structure was capable of being held in one hand. According to the patent, the described instrument is capable of assessing certain physical conditions such as the existence of severe emotional tension.

U.S. Pat. No. 3,834,374 to M. Ensanian describes an instrument said to be capable of diagnostic electrical scanning. A stationary electrode is placed in contact with the skin surface of the patient and then the body surface is scanned along a continuous path or over an area by rolling an exploratory electrode over the surface. This permits the instrument to map the potential along the line or over the area contacted by the exploratory electrode.

U.S. Pat. No. 3,870,034 which issued to Cyborg Corporation describes a device intended to be worn on one's wrist and capable of measuring the galvanic skin response of the wearer and thereby indicating the individual's tension level. The instrument houses an oscillator circuit, a battery, a sound emitting device and a pair of spaced electodes located on opposite ends of the instrument casing. In use the electrodes are touched by two fingers of the wearer to provide a reading of the tension level.

There are certain problems and difficulties encountered with use of some of the known devices for measuring an electrical characteristic of living tissue such as skin. Some of these known methods are considered unsafe, particularly in certain circumstances or with certain patients and they can be painful or otherwise invasive. The levels of test current required can be too high, particularly for some potential or known possible applications for these devices. Many of these known devices and methods require that the current pass through the body and this can cause undesirable effects on the body. Such effects may be so serious as to render the method too dangerous for general use, particularly on humans. As indicated earlier, some of the known methods require that the skin be punctured under one of the two electrodes with a needle or lancet set and this of course can cause discomfort. If electrically conductive creams or pastes must be used on the skin, there is a potential problem of a hypersensitive or allergic reaction in the patient.

It is an object of the present invention to provide a diagnostic device for assessing pain, abnormal sensation or sympathetic dysfunction in a human being or animal which avoids some or all of the aforementioned disadvantages and risks with the use of previously known instruments.

It is a further object of the present invention to provide a diagnostic device capable of operating on a low voltage power source, such as a battery and able to measure and quantify the level of conductance of living tissue such as human skin.

SUMMARY OF THE INVENTION

According to the invention, a diagnostic device for assessing pain, abnormal sensation or sympathetic dysfunction in a human being or animal includes a housing adapted to be held in a user's hand, two spaced-apart concentric electrodes mounted outside the housing for measuring conductance of human or animal tissue over a short distance and means for rigidly holding and supporting the electrodes said spaced-apart, concentric relationship. An electric circuit connected to the electrodes produces an electrical signal having a pulse frequency that varies according to the measured conductance. This electric circuit includes a voltage to frequency converter having an oscillator with logarithmic output so that the pulse frequency varies logarithmically according to the conductance measured by the electrodes. The logarithmic output permits a wide range of tissue conductance to be measured. A source of low voltage power, such as a battery, is connected to the electric circuit and means are provided for detecting the electrical signal to permit the user of the device to know the pulse frequency of the signal.

According to another aspect of the present invention, a diagnostic device capable of measuring the conductance of human or animal tissue includes a housing capable of being held in one hand by the user of the device and concentric electrode means mounted on the exterior of the housing. An electric circuit is located in the housing and is connected to the electrode means for producing an electrical signal having a pulse frequency that varies directly according to the conductance of human or animal tissue placed in contact with the electrode means. This electric circuit includes a voltage to frequency converter having an oscillator with logarithmic output so that the pulse frequency varies logarithmically according to the conductance measured by the electrodes. The logarithmic output permits a wide range of tissue conductance to be measured. A source of low voltage power is connected to the circuit means and means are provided for detecting the electrical signal to permit the user to know the pulse frequency of the signal. The latter means are arranged in the housing.

Ongoing clinical and control trials by the applicants have shown that the diagnostic instrument described herein can be used to great benefit in the objective, quantifiable assessment of human patients and animals with autonomic or pheripheral nervous system diseases, especially those which cause or accompany chronic pain. The major applications for the described instrument lie in the localization and confirmation of abnormalities which produce pain or paraesthesiae (pins and needles, itching, numbness) and differentiating organic causes of pain from so called "purely psychogenic" or "mental" causes of pain.

Further features and advantages will be apparent from the following detailed description, given by way of example, of a preferred embodiment taken in conjunction with the accompanying drawing.

DETAILED DESCRIPTION OF PREFERRED EMBODIMENT

Figures 1, 2:
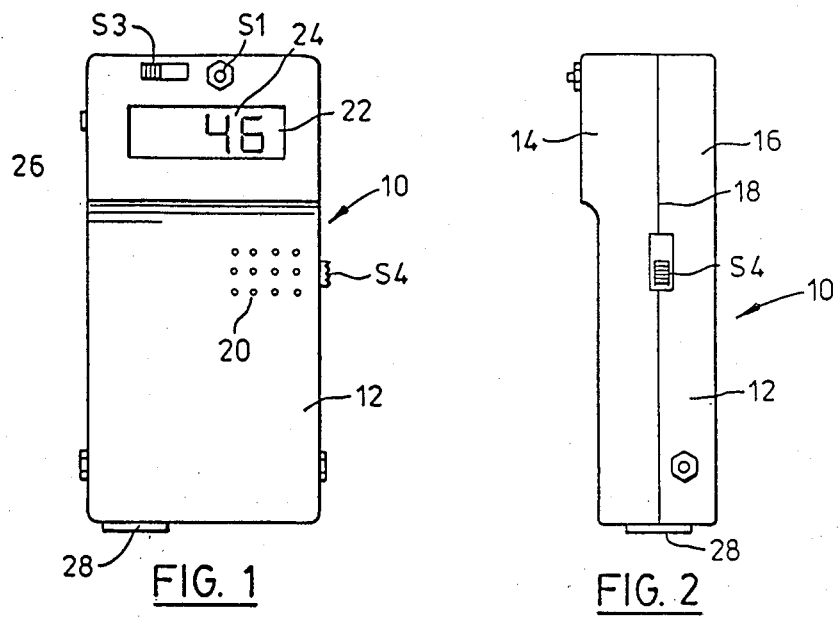
FIG. 1 is a front view of a diagnostic device constructed in accordance with the present invention.
FIG. 2 is a side view of the diagnostic device of FIG. 1.

The diagnostic device 10 of the present invention has an external housing 12 which in the illustrated embodiment is sufficiently small to be held in one hand by the user. The device could for example be approximately three inches wide and approximately six inches in overall length. The housing can be constructed from two parts comprising a front half 14 and a rear half 16 which separate along the line 18. The two halves can be held together by any suitable means such as small screws (not shown). The housing can be made from a strong plastic that is both shock resistant and water resistant. The housing should be electrically insulated from the electrical circuitry located in the housing, which circuitry is described hereinafter. Such methods of insulation are well known and need not be described further herein as the use of such insulation is well known in the construction of electrical instruments of this type.

The front of the case is provided with suitable openings 20 for the emission of sound from a small speaker in the housing. Located at the top end of the front is a digital display window 22 through which can be seen the digital readout of a three digit liquid crystal display 24. Also at the top end is a sliding on-off switch S3 by which the device 10 can be turned on in order to measure the conductance of tissue. Located beside this switch is a pushbutton S1 which enables the user to obtain a digital read out when the device is operating in the manual mode. Located on the left-hand side of the case is a plug 26 for an earphone jack, the use of which is explained further hereinafter.

Located on the right-hand side of the housing is a four position switch S4 by which the user can select the desired conductance range for the instrument.

Figures 3, 4:
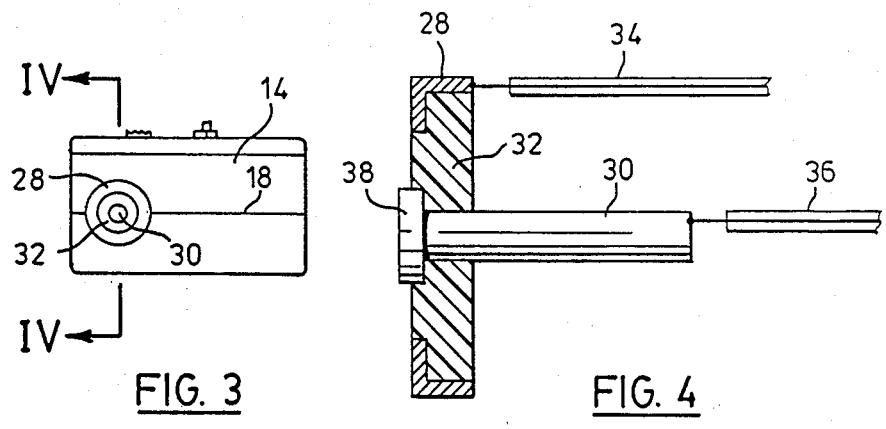
FIG. 3 is a bottom end view of the diagnostic device.
FIG. 4 is a sectional view of the concentric electrodes shown in FIG. 3 taken along the line IV—IV of FIG. 3.

Located at the bottom of the casing is the concentric electrode means of the diagnostic device. These means comprise an annular outer electrode 28 and an inner electrode 30. Preferably the two electrodes project from a side of the housing as shown in FIGS. 1 and 2. These electrodes are preferably made from chrome-plated brass which is non-corrosive and will not polarize. The two electrodes are separated by insulating material 32 which can consist of hard rubber joined to the electrodes by epoxy. The outer electrode 28 is the grounded side of the electrical circuit. As can be seen from FIG. 4, an insulated lead 34 extends from the outer electrode to the electrical circuit shown in FIG. 6 while an insulated lead 36 extends from the inner electrode 30 to the electrical circuit. It will be appreciated by those skilled in medical electronics that any electrically conductive material may be used for either the inner electrode or the outer electrode. Further any highly resistive or non-conductive material may be used for the spacer 32. It should also be appreciated that the central contact at 38, the spacer 32 or the outer electrode 28 can have any shape, such as that of a circle, oval, triangle, square, rectangle, or any other polygon. The surface area of the central contact, spacer, and outer electrode can also vary as can the contour thereof. The outer electrode can be complete or incomplete in its configuration. However it is preferred that the geometric centre of the central contact, the spacer, and the outer electrode should be common or identical and, within the context of the present specification and the claims of this application, the meaning of "concentric" is that the electrodes have a common or identical geometric centre.

Figure 5:
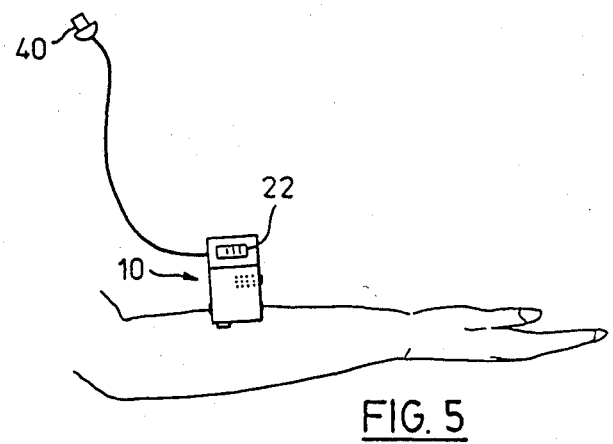
FIG. 5 is a schematic illustration showing how the device of FIG. 1 is used to obtain a tissue conductance reading.

FIG. 5 illustrates how the device 10 can be used to measure skin or tissue conductance in a human. The concentric electrodes are placed against the skin at the location where a measurement is desired. As explained hereinafter, the preferred device is capable of either providing a "click" readout in the form of an audible sound that is indicative of the level of conductance in the area where the measurement is being taken or a digital readout. The sound is emitted through the holes 20 or, if it is desired that the clicking sound only be heard by the doctor or user of the device, the jack of an earphone 40 can be plugged into the socket provided at 26. Also it is possible to have a digital readout of the conductance by viewing through the window 22.

Figure 6:
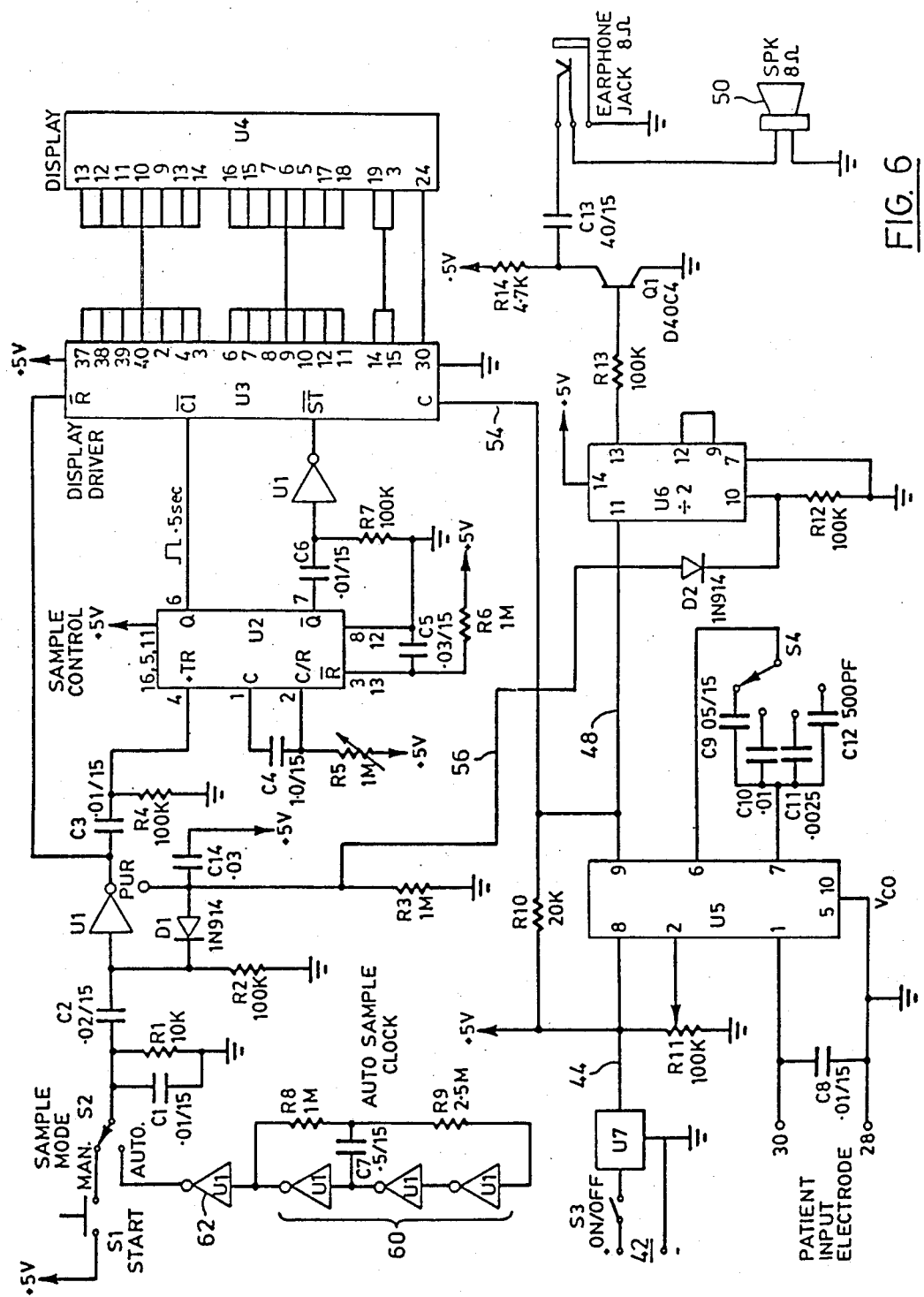
FIG. 6 is a diagram of the preferred electric circuit for the diagnostic device of the present invention.

Turning now to the circuit diagram as shown in FIG. 6, the location of the concentric electrodes in the circuit is shown in the bottom left-hand corner as is the source of low voltage power located at 42. In one particular preferred embodiment constructed by the applicants the source of power is a small nine volt battery capable of providing a low level test current that is below the sensory threshold. The electrical circuit is energized from the battery by closing the switch S3 referred to previously. A line from the switch S3 leads to a voltage regulator U7 which is connected by a line 44 to a voltage controlled oscillator U5. The regulator U7 can consist of a regulator number 78L05 while the oscillator U5 can comprise analogue device number AD537H. The oscillator U5 acts as an analogue device that converts voltage to frequency. In other words the oscillator U5 produces an output electrical signal having a pulse frequency that varies logarithmically according to the conductance measured by the concentric electrodes. A resistor R11 connected to line 44 and to oscillator U5 provides a bias adjust for U5 and sets up a control level which is set tentatively at one volt. Also connected to the line 44 and to a plus five volt power source is pullup resistor R10. This pullup resistor for the output of U5 establishes a normal plus five volt output which is then internally controlled and oscillated from U5.

Connected between the leads running from the two electrodes 28 and 30 to U5 is capacitor C8 which is a buffer used for input filtering. The aforementioned switch S4 permits the user to select between one of four capacitors C9, C10, C11 and C12, each of which is connected at one side of the oscillator U5. In the preferred embodiment each of these capacitors is rated for 15 volts. The size of each capacitor is indicated in FIG. 6 and ranges from 0.5 microfarads for C9 to 500 picofarads for C12. A line 48 connects the oscillator U5 to U6 which is a R.S. flip-flop used as a frequency divider. The flip-flop U6 can be type 4013 and it is connected to a plus five volt power source. The flip-flop U6 divides the frequency of the electrical signal coming from U5 by two. The output from U6 then goes out through a standard speaker drive to either the earphone 40 or a small 8 ohm one inch speaker 50 to provide a "click" read out. The speaker drive is formed from resistor R13 and R14, a capacitor C13 and transistor Q1 which can be type D40C4. The resistor R13 is a biasing control for Q1 and it establishes a maximum current level through the base. It also acts to protect U6 from a shorted Q1 base emitter junction. The resistor R14 which is connected to the +5 volt power source is a loading resistor while the capacitor C13 is an A.C. coupler.

Connected to the pin 10 of flip-flop U6 is a resistor R12 and an isolating diode D2 which can be type IN914. The resistor R12 ties the PUR to ground and acts as a bias resistor. The diode D2 also acts as a coupler to couple the PUR (power up reset) to the reset line of U6 and, after the PUR function, D2 isolates the reset line of U6. On the initial switching on of the device, the PUR guarantees that all components of the device are in the proper electronic states.

Figure 7:
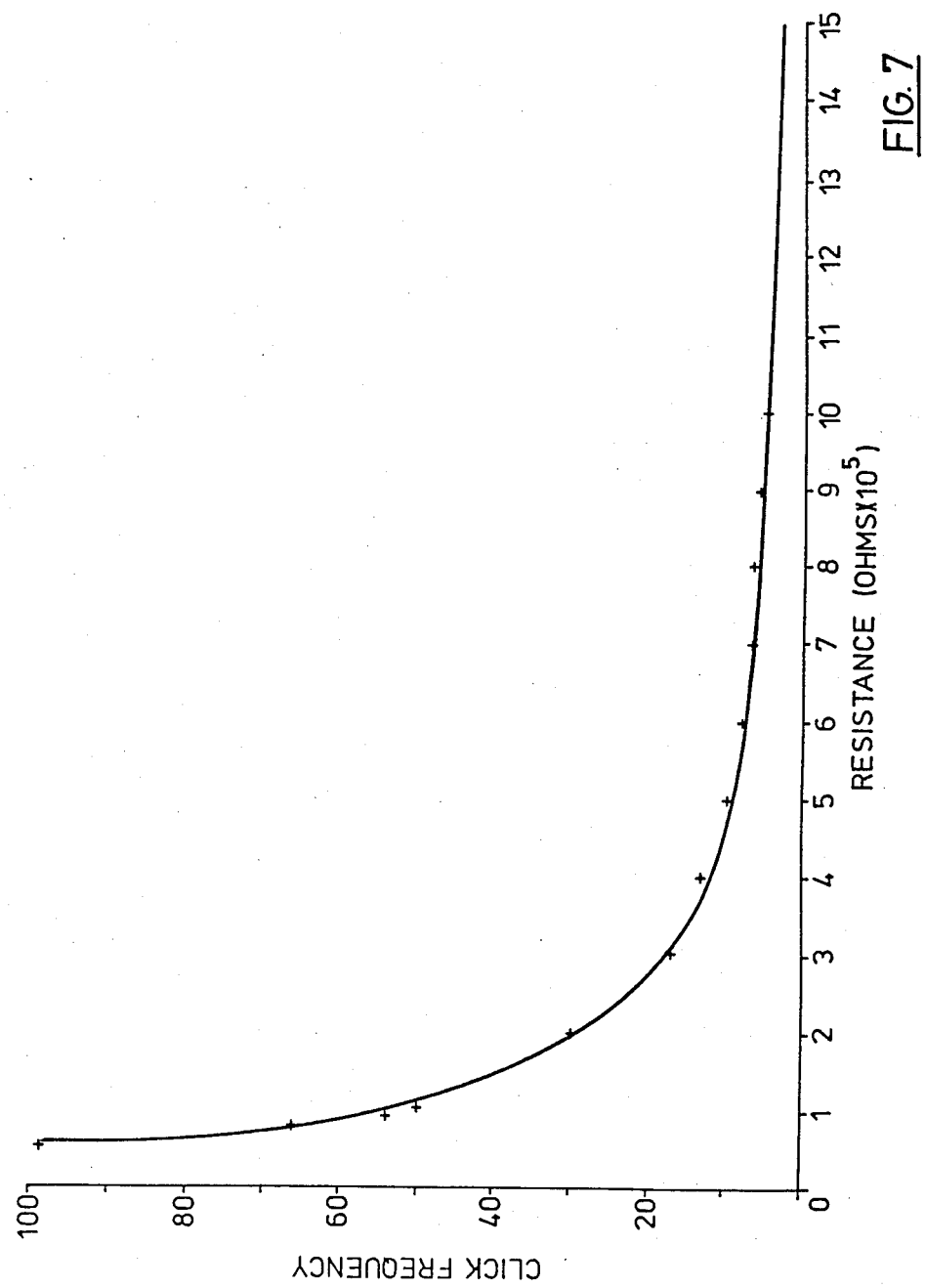
FIG. 7 is a graph illustrating the relationship between tissue or skin resistance and click frequency.

It should be appreciated that the above described electrical circuit is sufficient for a working embodiment if all that is required by the user is an audible indication of the level of conductance. With this electrical circuit, each pulse coming from the output of U6 will be presented as an audible "click" sound either over the earphone or through the speaker 50. The relationship between the click frequency and the level of resistance (using calibration resistors) is illustrated in FIG. 7 of the drawings. As can be seen from the graph, as the resistance approaches zero the click frequency becomes very high reaching 100 or more. However if the resistance is increased to a very high level, the click frequency fall to 2 clicks per second or less. With applicant's device however, it is the conductance of the skin that is measured and not resistance. Accordingly as the conductance of the skin increases, the number of clicks produced will increase. It is believed that the use of conductance as the electrical characteristic to be measured has a distinct advantage over the use of resistance because the relationship between conductance and the click frequency or digital read out is a direct relationship rather than an inverse relationship. Accordingly applicant's device is easier to use, particularly for one who has not considerable experience with the device, than earlier devices that measured resistance.

The preferred embodiment of the present invention provides an alternative or additional means for monitoring or measuring the electrical signal coming from the oscillator U5. Preferably the measuring means consists of a liquid crystal display U4 which can be type 3940 made by Hamlin and a counter and display driver U3. The display driver U3 can be type ICM7224 made by Intersil. It is connected to the oscillator U5 by means of lead 54. Also connected to the lead 54 is 20K resistor R10 which as indicated above is a pullup resistor for the output of the voltage controlled oscillator U5.

The illustrated digital display circuit can operate either on a manual mode or an automatic mode, the selection being made by means of switch S2. The switch S2 can be located on top of the housing 12 if desired. In the manual mode, in order to obtain a digital read out on U4, the user must engage the push-button S1. With the automatic mode, which is described further hereinafter, the readout is produced automatically after the elapse of a set time interval. The push-button switch S1 capacitor C2 and resistor R2 establish a two millisecond pulse to the inverter U1 which inverts the function and produces a two millisecond negative excursion pulse. The component U1 can be type 40106. Connected between the switch S2 and the inverter U1 are capacitors C1 and C2 and a 10K resistor R1. The capacitor C1 is an input filter which clears the display driver U3.

Returning to the output of U1, a capacitor C3 and a 100K resistor R4 create a one millisecond positive pulse, on the positive going slope of the aforementioned two millisecond pulse. The one millisecond pulse triggers the + trigger input of component U2, which is a monostable multivibrator, and U2 then puts out one pulse the width of which is controlled by the capacitor C4 and a resistor R5. The resistor R5 is adjustable so that the pulse width can be set at 500 milliseconds. The multivibrator U2 can be type 4538 and the function of this component is to allow a half second time interval during which U3 can count the pulses of the electrical signal. The lines from pins 6 and 7 of component U2 are each provided for the control of the "count inhibit" and "store" functions of U3. The signal passing through pins 6 and 7 of U2 are inverse of one another. The indicated symbol Q at pin 6 represents a normally rising function while the symbol $\overline{Q}$ represents a represents a normally falling function. The function Q is the count inhibit time for U3 and in applicant's preferred embodiment this time is 0.5 seconds. Thus passing from pin 6 is a positive going ½ second pulse while passing from pin 7 is a negative going ½ second pulse. With respect to the latter, on the positive slope of the wave, a capacitor C6 and resistor R7 create a one millisecond pulse which is inverted by U1 to create a one millisecond falling pulse. The latter pulse is fed to the store input of U3 which latches and stores the accumulated count over the ½ second time period. At the end of the time period, the three digit display is updated with the new count information.

Also connected to component U2 are a capacitor C5 and a 1.0 megohm resistor R6 which provide a power up reset (PUR) for U2 by providing a 30 millisecond delay on turn on. This delay holds the reset of U2 at "0" volts for 30 milliseconds after which a +5.0 volt level is applied and maintained. Connected to a lead 56 which runs to the isolator D2 is a 1.0M resistor R3 and a capacitor C14. These components provide a power up reset for the display driver U3 and component U6. The display drive U3 is reset through a diode D1 which can be type IN914, and the inverter U1. The component U6 is reset through the isolator D2.

Turning now to the additional components required in the display circuit for the automatic mode of operation, three U1 componets designated 60 on FIG. 6 are provided to form a free running oscillator. These components are connected to a 1.0M resistor R8 and a 2.5M resistor R9 which also form part of this oscillator. Connected between the two resistors R8 and R9 and between two of the components U1 is a capacitor C7. The oscillator produces a five volt, one hertz square wave which runs all the time. A fourth component U1 indicated at 62 is a buffer used to couple the one hertz signal to the input of C2 through the switch S2. Every time the capacitor C2 reaches the positive going slope of the one hertz signal, the manual sequence which has already been explained is repeated. Thus in the automatic mode the three digit liquid crystal display is updated with the latest pulse frequency after a set time interval.

With reference to FIG. 6 of the drawings, it should be noted that all resistors are ⅛ W and 1% tolerance and all capacitors are in mirofarads unless otherwise specified.

The ability of the preferred diagnostic device described herein to measure the conductance of tissue or skin over a wide range is a significant advantage as the conductance of such material will vary widely. Using the capacitors C9, C10, C11, and C12 at the switch S4 indicated in FIG. 6 will provide for different conductance ranges, namely 0.1 to 1 micromhos, 0.5 to 5 micromhos, 2 to 20 micromhos and 10 to 100 micromhos.

Another feature which gives the present conductance meter the wider range which is necessary in the context of assessing pain, abnormal sensation or sympathetic disfunction is the lagarithmic scale employed in the meter. In otherwords the output electrical signal from the oscillator U5 is a logarithm of the input which is a measure of conductance. Previous meters have not provided for a logarithmic output with the standard previous scale being linear. It should be noted that the current consumption of the preferred device is very low, typically 5.1 milliamps. At the most (worst case situation) the consumption could reach 8.3 milliamps. The maximum current through the electrode is 100 microamps but electrode current is normally much less than this amount.

It will be obvious to those skilled in the art that various modifications and changes can be made to the described embodiment without departing from the spirit and scope of this invention. Accordingly all such modifications and changes as fall within the scope of the appended claims form part of the present invention.

What I claim as my invention is:

1. A diagnostic device for assessing pain, abnormal sensation or sympathetic dysfunction in a human being or animal comprising:
   a housing adapted to be held in a user's hand;
   two spaced-apart, concentric electrodes mounted outside said housing for measuring conductance of human or animal tissue over a short distance;
   means for rigidly holding and supporting said electrodes in said spaced-apart, concentric relationship;
   electric circuit means connected to said electrodes for producing an electrical signal having a pulse frequency that varies directly according to said measured conductance, said circuit means including a voltage to frequency converter having an oscillator with a logarithmic output so that the pulse frequency of said electric signal varies logarithmically according to the conductance measured by said electrodes, said logarithmic output permitting a wide range of tissue conductance to be measured by said device;
   a source of low voltage power connected to said circuit means; and
   means for detecting said electrical signal to permit the user of said device to determine the pulse frequency of said signal.

2. A diagnostic device according to claim 1 wherein said voltage to frequency converter is connected to means for providing two or more conductance ranges.

3. A diagnostic device according to claim 2 wherein said means for providing two or more conductance ranges comprise two or more capacitors and a switch capable of being moved between two or more operating positions so as to connect one of said capacitors into the electric circuit at each position.

4. A diagnostic device according to claim 1 wherein said means for detecting said electrical signal comprises an audio circuit that in operation produces an audible sound or click sound for each pulse of said electrical signal.

5. A diagnostic device according to claim 1 wherein said electrodes are made of chrome plated brass and said electrode holding means comprises non-conducting rubber and epoxy.

6. A diagnostic device according to claim 1 wherein said device is small enough to be held in one hand by the user and said source of power is a battery.

7. A diagnostic device according to claim 1 wherein said electric circuit further includes means for dividing the frequency of the pulses of said electrical signal, said dividing means being electrically connected to said oscillator, a voltage regulator electrically connected to said oscillator, and a switch for connecting or disconnecting said source of power, said switch being connected between said source of low voltage power and said voltage regulator.

8. A diagnostic device according to claim 1 wherein said detecting means comprises means for providing a digital display of the frequency of the pulses of said electrical signal.

9. A diagnostic device according to claim 8 wherein said display providing means comprises a pulse counter and display driver, a timer to permit the pulse counter to countup over a selected time interval, said timer being electrically connected to said pulse counter and display driver, and a digital display unit electrically connected to said pulse counter and display driver.

10. A diagnostic device according to claim 9 wherein said display providing means includes means for selecting between an automatic mode of operation and a manual mode of operation and wherein, in said automatic mode, said display providing means generates a new or updated digital readout automatically after a set period of time has elapsed and in said manual mode, the user of the device is required to operate a switch in order to have a digital readout generated.

11. A diagnostic device according to claim 1 wherein said electrodes project from a side of said housing a short distance.

12. A diagnostic device capable of measuring the conductance of human or animal tissue comprising:
 a housing capable of being held in one hand by the user of said device;
 concentric electrode means mounted on the exterior of said housing;
 electric circuit means located in said housing and connected to said electrode means for producing an electrical signal having a pulse frequency that varies directly according to the conductance of human or animal tissue placed in contact with said electrode means, said circuit means including a voltage to frequency converter having an oscillator with a logarithmic output so that the pulse frequency of said electric signal varies logarithmically according to the conductance measured by said electrode means, said logarithmic output permitting a wide range of tissue conductance to be measured by said device;
 a source of low voltage power connected to said circuit means; and
 means for detecting said electrical signal to permit the user of said device to know the pulse frequency of said signal, said detecting means being arranged in said housing.

13. A diagnostic device according to claim 11 wherein said power source is a battery located in said housing.

14. A diagnostic device according to claim 11 wherein said electrode means comprises two electrodes separated by and held in concentric relationship by an electrically insulating, solid material.

15. A diagnostic device according to claim 13 wherein said means for detecting said electrical signal comprises means for providing a digital display of the frequency of the pulses.

16. A diagnostic device according to claim 12 wherein said voltage to frequency converter is connected to means for providing two or more conductance ranges.

17. A diagnostic device according to claim 16 wherein said means for providing two or more conductance ranges comprises two or more capacitors and a switch capable of being moved between two or more operating positions so as to connect one of said capacitors into the electric circuit at each position.

18. A diagnostic device according to claim 12 wherein said means for detecting said electric signal comprises an audio circuit that in operation produces an audible sound or tone for each pulse of said electrical signal.

19. A diagnostic device according to claim 18 wherein said audio circuit includes a small speaker mounted in said housing.

20. A diagnostic device according to claim 19 wherein said audio circuit has means for connecting an earphone to said circuit and wherein connection of said earphone to said audio circuit stops operation of said speaker.

* * * * *